Figure 3:
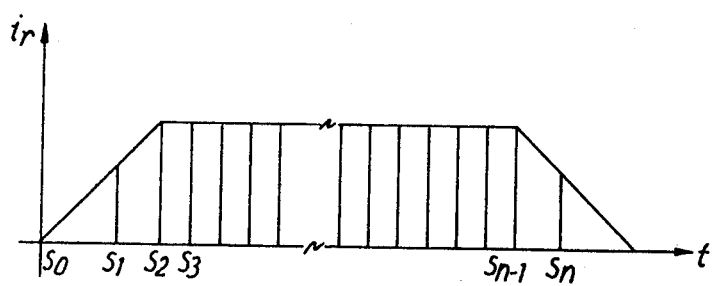

United States Patent [19]

Young et al.

[11] 4,384,255

[45] May 17, 1983

[54] NUCLEAR MAGNETIC RESONANCE SYSTEMS

[75] Inventors: Ian R. Young, Sunbury-on-Thames, England; Colin G. Harrison, San Jose, Calif.

[73] Assignee: Picker International Limited, Wembley, England

[21] Appl. No.: 175,673

[22] Filed: Aug. 5, 1980

[30] Foreign Application Priority Data

Aug. 10, 1979 [GB] United Kingdom ................. 7927974

[51] Int. Cl.³ ............................................. G01R 33/08
[52] U.S. Cl. ..................................... 324/309; 324/312
[58] Field of Search ............... 324/300, 307, 309, 310, 324/311, 313, 320

[56] References Cited

U.S. PATENT DOCUMENTS

| | | | |
|---|---|---|---|
| 2,700,147 | 1/1955 | Tucker | 324/312 |
| 3,048,772 | 8/1962 | Saunders et al. | 324/310 |
| 3,443,209 | 5/1969 | Nelson et al. | 324/320 |
| 4,021,726 | 5/1977 | Garroway | 324/309 |
| 4,300,096 | 11/1981 | Harrison | 324/309 |

Primary Examiner—Michael J. Tokar
Attorney, Agent, or Firm—Fleit, Jacobson & Cohn

[57] ABSTRACT

The invention concerns the production of gradient fields for nuclear magnetic resonance apparatus particularly imaging apparatus. It has been earlier proposed that samples of the resonance signal be taken at intervals such that the field gradient integrals in each such interval are the same. This sampling is at unequal time intervals. It is now proposed to provide the gradient fields in discrete pulses with spaces in between at which samples can be taken. It is then straightforward to make the pulses of equal field integral or to provide an extra small pulse in one or both of the orthogonal gradients if the field integral should need adjusting before the next sample.

10 Claims, 9 Drawing Figures

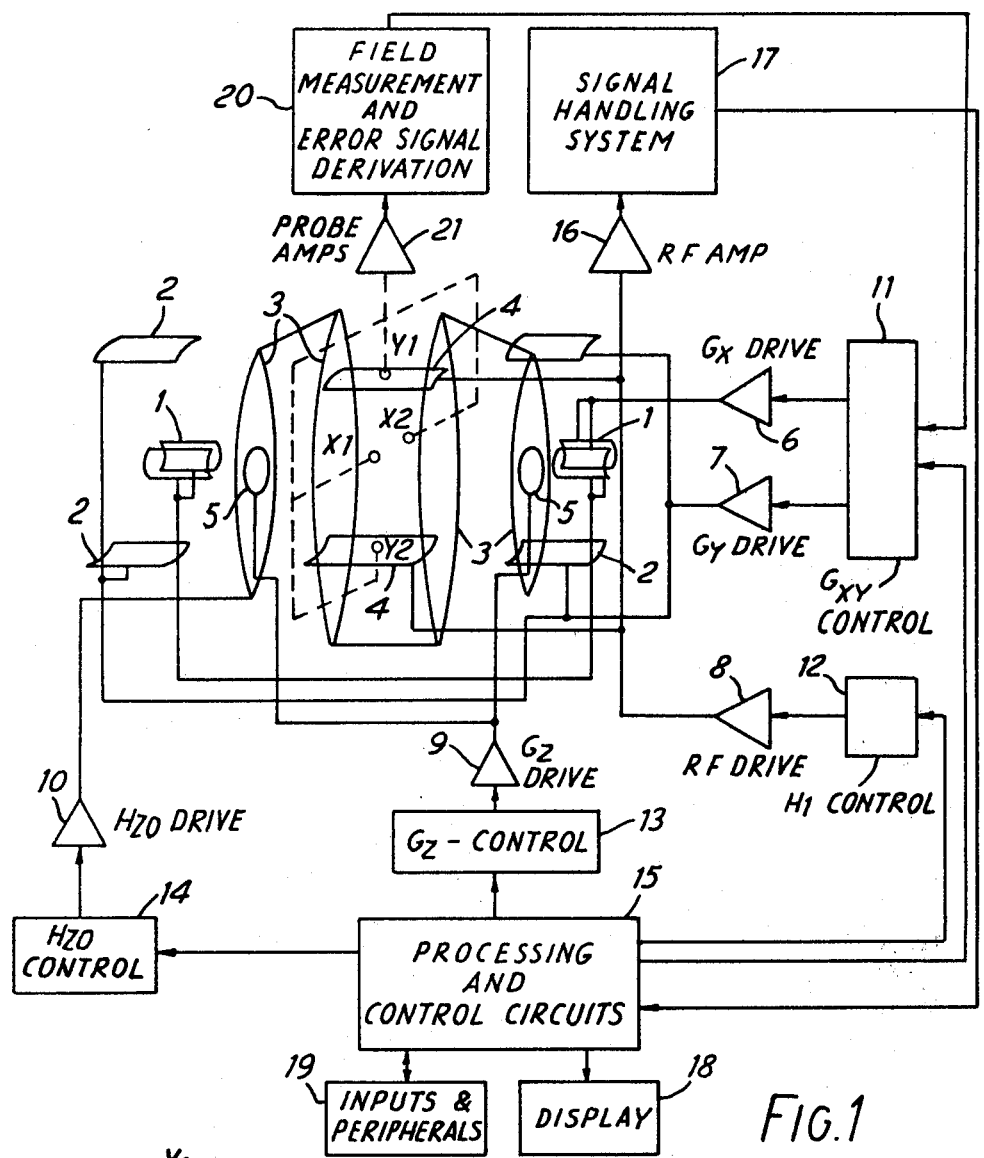
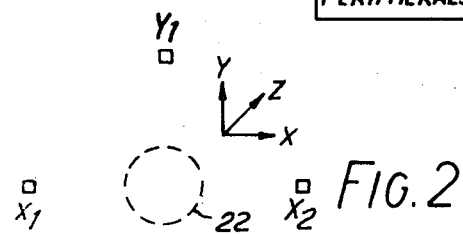
FIG.1
FIG.2

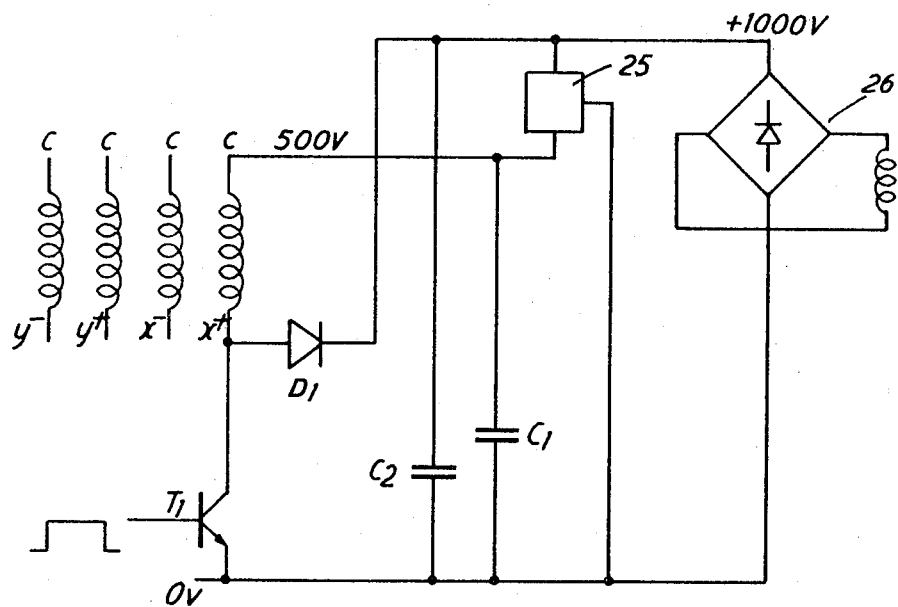
FIG.6
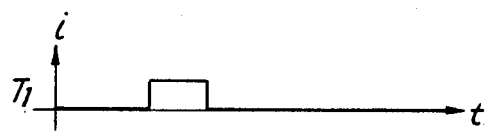
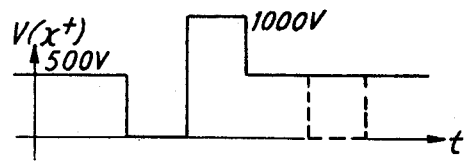
FIG.7
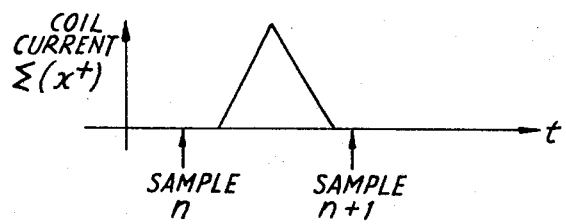

NUCLEAR MAGNETIC RESONANCE SYSTEMS

The present invention relates to systems for providing, by nuclear magnetic resonance, images of distributions of a chosen quantity in a selected region of a body. The examination may be of many different kinds of bodies but a particularly beneficial application, to which much attention has been given, is the medical examination of patients.

Nuclear Magnetic Resonance (NMR) is now well known for the examination of materials by spectroscopy. For medical examination it has been proposed to use variations of the technique to provide distributions of, for example, water content or relaxation time constants in sectional slices or volumes of patients. Such distributions are similar to the distributions of x-rays provided by computerised tomographic (CT) systems, although they have different significance.

For NMR examination, suitable combinations of magnetic fields are applied to the body to be examined by appropriate magnet (coil) systems. The resonances which are caused are then detected as induced currents in one or more detector coil systems and are analysed to provide the required distribution.

Several proposals have been made for apparatuses to achieve this and for field pulse sequences to operate them, for example the methods and apparatus described in U.S. Pat. Nos. 4,315,216; 4,254,778; 4,284,948; 4,300,096; and 4,284,950.

Such methods involve selection of a planar slice of interest, in the body, which may be by inducing resonance preferentially in the slice. It has then been proposed to apply a field which is perpendicular to the slice (direction z) but which has a gradient in one direction (r) in the slice. This is generally achieved by the use of field gradients in two orthogonal directions (x and y) in the slice, the direction of r being variable by varying the relative amplitudes of the x and y fields. The effect of this field gradient ($G_R = H_z/r$ where $H_z$ is the field in the z-direction, generally the body longitudinal axis) is to introduce a dispersion of the nuclei resonance frequencies in the r direction. Resonance signals then detected can be distinguished as being for a plurality of linear strips in the slice perpendicular to the r direction. Repetition of the procedure for different r directions can give many such signals for strips in many different directions in the slice. These are similar to the x-ray attenuation signals provided by the well known CT systems for x-ray beams and they may be analysed by the methods well known in CT with some appropriate changes.

The gradient fields may be provided in different ways and may have different waveforms. One proposal has been to use thyristor circulating current through a tuned circuit. The waveforms which result are often sinusoids in intent, although they are distorted for example by quality of the coils, adjacent metal including parts of the magnets etc. Other shapes can be used and these will also clearly be affected by the same distortions.

In U.S. Ser. No. 39,650 it has been suggested that, as the gradients develop and the spins of nuclei across the slice fall out of phase, sampling of the resonance signals is required at unequal intervals of time so that the gradient field integrals in each such interval are equal. Such sampling, properly achieved can be correct even with distorted fields. Problems with obtaining the field waveforms and the above requirement of sample timing can, however, require quite complex field measuring and control systems.

It is an object of this invention to provide an alternative gradient field system.

According to the invention there is provided a method of examining a body by nuclear magnetic resonance, including: the application of magnetic fields to induce resonance preferentially in a slice of the body; the application of one or more field gradients in the slice to induce a dispersion of the resonance frequencies in a chosen direction in the slice; measurement of resonance signals from the slice at intervals during the applications of the field gradient, the total field integral of the gradient component at any point being substantially equal between successive samples; wherein the field gradient is applied as a sequence of discrete pulses with intervals of substantially zero field gradient intensity between adjacent pulses and the resonance signals are sampled during at least some of the said intervals.

The invention embraces apparatus for implementing the above method.

Figure 4:
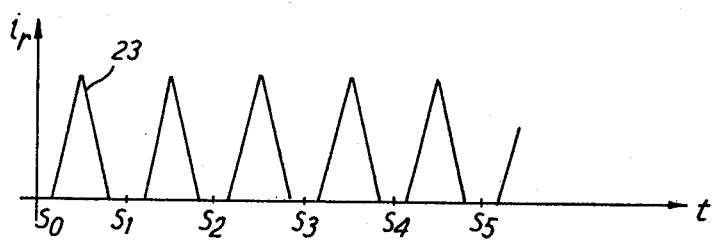
Figure 5A:
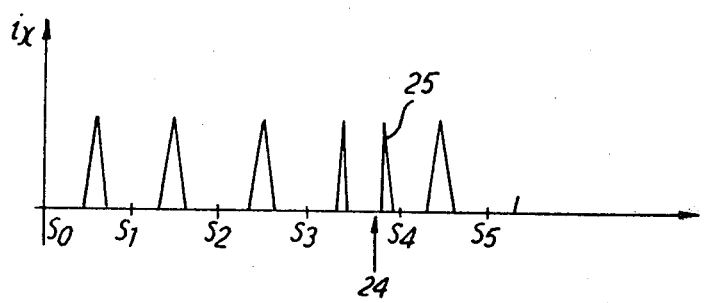
Figure 5B:
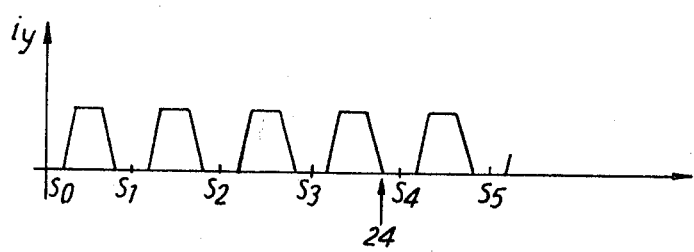
Figure 8:
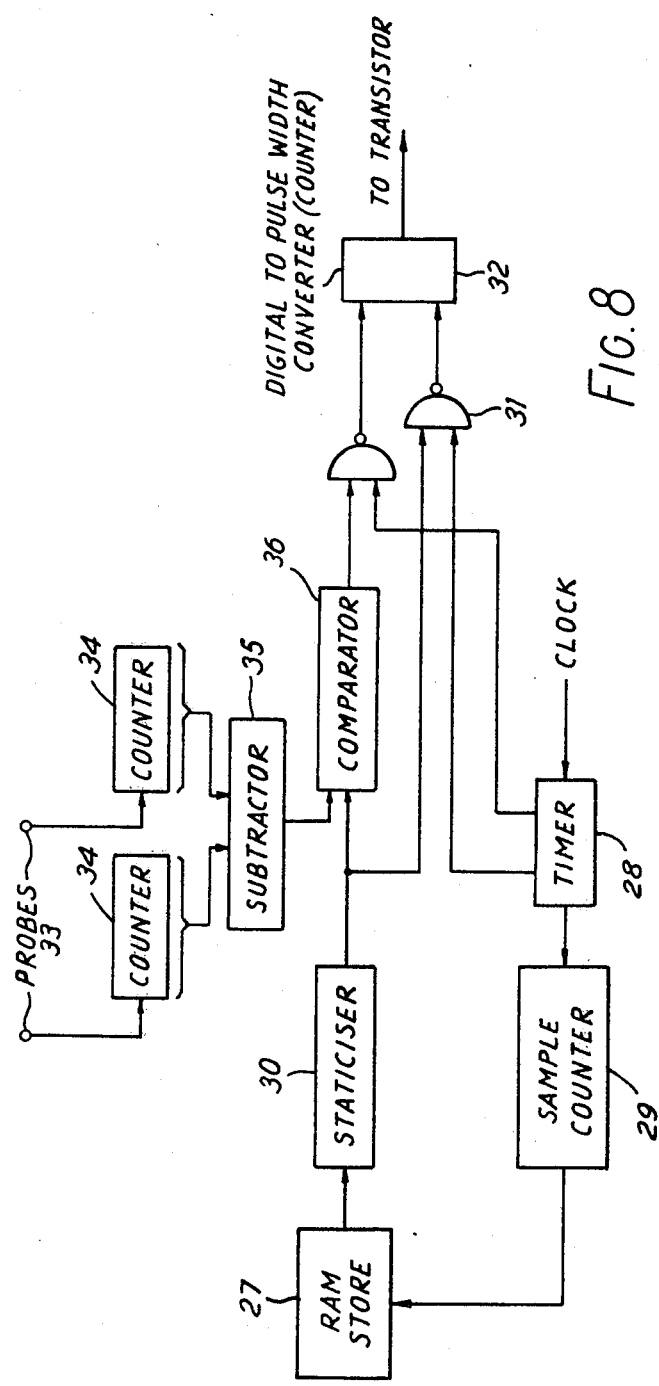

In order that the invention may be clearly understood and readily carried into effect it will now be described with reference to the accompanying drawings of which, FIG. 1 shows an NMR apparatus with which the invention may be used, FIG. 2 shows a distribution of field sensing probes for that apparatus, FIG. 3, shows the previously proposed field gradient and sampling timing, FIG. 4 shows gradient field pulses and sample timings for this invention, FIGS. 5a and 5b show respectively x and y pulses as in FIG. 4 showing how the invention facilitates correction, FIG. 6 shows a circuit for applying the coil currents, FIG. 7 shows some voltages and currents for the circuits of FIG. 6, and FIG. 8 shows a circuit for controlling operation of the transistor switch 4 of FIG. 6.

FIG. 1 shows in simplified form the NMR apparatus described in the said applications. Illustrated, schematically only, are coils 1, which provide the Gx component of $G_R$, 2, which provide the Gy component of $G_R$, 3, which provide a steady $H_{zo}$ field, 4, which provide a rotating $H_1$ r.f. field, and 5, which provide a $G_z$ field gradient. The coils are driven by Gx, Gy, RF ($H_1$), $G_z$ and $H_{zo}$ drive amplifiers 6, 7, 8, 9 and 10 respectively, controlled by $G_{xy}(G_R)$, $H_1$, $G_z$ and $H_{zo}$ control circuits 11, 12, 13 and 14 respectively. These circuits can take suitable forms which will be well known to those with experience of NMR equipment and other apparatuses using coil produced magnetic fields. The circuits are controlled by a central processing and control unit 15 to achieve a desired pulse sequence.

The signal sensed, during the $G_R$ field application, is received in this example by the $H_1$ coils 4 and is amplified by an RF amplifier 16 before being applied to signal handling circuits 17. In certain circumstances it may be preferable to provide separate coils specifically designed for the purpose, to sense the signal. The circuits 17 are arranged to make any appropriate calibrations and corrections but essentially transmit the signals to the processing circuits to provide the required representation of the examined slice. These circuits can be specially designed to Fourier transform the signals and then to implement CT type processing for example as described and claimed in British Pat. No. 1,471,531, since the transformed signals are, in effect, proton density values for strips in the body. It is, however, advantageous to implement the processing by a suitably programmed digital computer. This computer can also conveniently control the pulse sequence and thus represents the circuits indicated at 15. The picture thus obtained is viewed on a display 18, such as television monitor, and this may include inputs and other peripherals 19 for the provision of commands and instructions to the machine, or other forms of output.

The apparatus also includes field measurement and error signal circuits 20 which receive signals via amplifiers 21 from field probes $X_1$, $X_2$, $Y_1$, $Y_2$, shown. The positions of the probes, in relation to the examined slice of the body 22 of the patient, are further shown in FIG. 2. The probes, are in this example, NMR probes which are simply miniature cells of pure or selectively doped water (such as a closed test tube) each surrounded by a small coil. Preferably the water is doped to have a suitable value of $T_1$ relaxation time-constant. The probes give a reliable resonance of 4.26 $kH_z/Oe$ and the field measured is provided by a suitable count. Other types of probe may be used as desired.

FIG. 3 shows the previous proposal for $G_R$ field generation. The Figure shows a plot of current through the field coils, which is proportional to the field generated, as a function of time. The field pulse illustrated is flat topped but the system embraces other shapes. Also shown are illustrative signal sampling times So to Sn having equal field integrals therebetween. As described in the principal embodiment of U.S. Ser. No. 39,650 the sampling for such a waveform could be achieved by measuring the field integral on-line and sampling at suitable values. Of course the equivalent technique of precalculating the equal integral sample times is also described. The intermediate technique of measuring the field (perhaps with a phantom body) at equal times, integrating the measurements, determining equal field sampling times and storing these in a look-up table for the actual examinations, is clearly equivalent.

In FIG. 4 there is shown the alternative proposal provided by this invention. This is achieved by switching the field current with, for example transistor switches to provide an individual current (and field) pulse 23 between each sampling time. The pulses are chosen to have the appropriate field integral between samples. It is effected merely by turning on the transistors and waiting for a precalculated time before turning them off.

As mentioned, the r-direction gradient is effected by x and y direction gradients whose relative amplitudes are varied. The present invention allows this by having different on and off times for the x and y field currents to give the appropriate relative amplitudes and the correct total field integral. This is illustrated in FIG. 5 where the x-field pulses are shown in FIG. 5(*a*) and the y field pulses, of greater duration as illustrated, are shown in FIG. 5(*b*).

An important point to understand is that, assuming that the uniformity of the steady $H_z$ field is sufficiently good, there is no further relative precession of the nuclei in the absence of the field gradient. Thus the field integral between samples can be adjusted to give the correct total and the sample taken with the gradient off. Provided the total reaches its correct value before the next sample there are no problems. Thus errors detected by the field measurement probes can be corrected before the next sample is taken.

For example, referring to FIG. 5, if at point 24 it is found that there is a relative error between the x and y gradients, an additional pulse 25 can be inserted before the next sample for correction. The next sample can be delayed to allow this, if necessary.

A further consequence of the absence of gradient at sampling is that several samples can be taken after each field integral increment to average noise.

It should be noted that this method increases the power requirement and, since voltages must be kept down to stay within transistor ratings as di/dt should be high, L must be kept low for the coils so that current requirements are consequently high.

The method can be used in conjunction with the method shown in FIG. 3, to give correction only and not full control, but that is not preferred.

FIG. 6 shows a circuit for the invention. For each direction of gradient coil ($\pm x$ and $\pm y$) there are two windings, one for each direction of field and these have identical coils and circuits. Consequently FIG. 6 only shows one circuit in full.

A high voltage switching transistor $T_1$ switches on for the required period, say 50 microseconds and the voltage on a capacitor $C_1$ drops by 500 volts to 0 volts. $T_1$ then switches off and the collector voltage increases to 1000 V. $D_1$ current causes the voltage on a capacitor $C_2$ to increase and the voltage on $C_1$ to decrease by 500 volts again. A series regulator 25 makes up the loss of voltage across $C_1$ by current from $C_2$ and the power supply 26. The currents and voltages resulting are shown in FIG. 7.

The average value or maximum current is controlled by the on/off ratio or the on time of the transistor. This is set by a central control to a preset pulse or by the field probe circuits if the pulses obtained are not correct.

Control of the transistor switch of FIG. 6 may be by a suitable circuit such as that shown in FIG. 8. Referring to that Figure, a Random access memory (RAM) store 27 holds the precalculated gradient integral values required between successive samples at each stage of the examination procedure. A timer 28, operating in response to input clock pulses is preprogrammed in conventional manner to produce output pulses on respective lines at appropriate clock counts. One output is to a sample counter 29 which simply counts the samples achieved and at appropriate preset stages in the sequence provides an address to RAM 27 to provide the required gradient field value. This value, which is for the expected pulse 23 (FIG. 4), is held in a staticiser 30 until it is replaced by the next value.

When a sample has been taken, which as indicated is arrived from the current count but may be indicated by an input pulse from the sampling circuits, the timer 28 sends a pulse to enable a gate 31 which passes the (digital) value of the gradient field. This is passed to a counter 32, operating in known manner as a digital to pulse width converter. The pulse of appropriate width is then output to the transistor switch to produce the required gradient pulse.

During this pulse two NMR probes 33, preferably equally spaced about the gradient zero, provide with counters 34 a measure of the fields at their locations and these are subtracted in a subtractor 35 to provide a value of the field gradient. This is compared in a comparator 36 with the required gradient value in staticiser 30 to determine and provide a value of any error in the first pulse shortly afterwards timer 28 opens a gate 37 which provides the error value to counter 32 to produce, if required, a correcting pulse 25 (FIG. 5a). In general a single correcting pulse would suffice but if desired the circuit of FIG. 8 can readily be adapted to repeat the correction procedure.

Other variations of the invention will be apparent to those with the appropriate skills.

What we claim is:

1. A method of examining a body by nuclear magnetic resonance, including: applying magnetic fields to induce resonance preferentially in a slice of the body; subsequently applying at least one further magnetic field having a gradient in a chosen direction in the slice to induce a dispersion of the resonance frequencies in said chosen direction in the slice; and measuring resonance signals from the slice at intervals during the applications of the field gradient, the total field integral of the gradient component being substantially equal between successive samples; wherein the field gradient is applied as a sequence of discrete pulses with intervals of substantially zero field gradient intensity between adjacent pulses, and the resonance signals are sampled during at least some of the said intervals.

2. A method according to claim 1 wherein at least one additional pulse is included between some of said samples to correct the field integral for field errors.

3. A method according to claim 1 or claim 2 wherein a plurality of samples are taken during each of the said at least some intervals to reduce the effects of noise thereon.

4. A method according to claim 1 wherein there are provided two field gradients of variable magnitudes in orthogonal directions to induce dispersion in a resultant direction which is said chosen direction, and the relative pulse magnitudes of substantially coincident pulses of the two gradients are varied to change the resultant direction.

5. An apparatus for examining a body by nuclear magnetic resonance, the apparatus comprising means for preferentially inducing resonance in nuclei in a slice of the body; means for applying a plurality of pulses of a magnetic field having a gradient in a chosen direction in the slice to include a dispersion of the resonance frequencies in said chosen direction, and with intervals of substantially zero field gradient intensity between adjacent pulses; and means for measuring resonance signals from said nuclei in at least some of said intervals such that the total field integral of the said field is substantially equal between successive measurements.

6. An apparatus according to claim 5 wherein the means for applying the magnetic field includes means applying two component magnetic fields having gradients in orthogonal directions in said slice, said gradients having a resultant providing the first mentioned magnetic field, and means for varying the magnitude of substantially coincident pulses of the two field components to vary the direction of the resultant field.

7. An apparatus according to claim 5 or claim 6 wherein the means for applying the magnetic field includes at least one transistor which is switch-controlled to switch the field on and off.

8. An apparatus according to claim 7, including at least one transistor switch for each of said component fields, and means for varying on and off times of said switches to vary the relative magnitudes of said coincident pulses.

9. An apparatus according to claim 5, including means for inserting additional pulses between measurements of resonance signals to adjust said field integral.

10. An apparatus according to claim 5 wherein the means for measuring is arranged to take a plurality of samples of the resonance signals for each measurement.

* * * * *